United States Patent
Plank et al.

(10) Patent No.: US 7,530,707 B2
(45) Date of Patent: May 12, 2009

(54) SEMICONDUCTOR RADIATION SOURCE

(75) Inventors: Wolfgang Plank, Rankweil (AT); Bruno Senn, Buchs (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 11/728,251

(22) Filed: Mar. 23, 2007

(65) Prior Publication Data

US 2007/0230208 A1 Oct. 4, 2007

(30) Foreign Application Priority Data

Apr. 3, 2006 (DE) ................. 10 2006 015 336

(51) Int. Cl.
*A61C 3/00* (2006.01)

(52) U.S. Cl. ............... 362/230; 362/800; 362/804

(58) Field of Classification Search ............ 362/800, 362/572, 573, 230, 231, 804
See application file for complete search history.

(56) References Cited

U.S. PATENT DOCUMENTS

| | | | |
|---|---|---|---|
| 4,568,558 A | 2/1986 | Angrick | |
| 6,866,506 B2 | 3/2005 | Plank et al. | |
| 7,210,930 B2 * | 5/2007 | Kovac et al. | 433/29 |
| 2002/0001192 A1 | 1/2002 | Suchiro et al. | |
| 2002/0177099 A1 | 11/2002 | Cao | |
| 2003/0053310 A1 | 3/2003 | Sommers | |
| 2004/0026683 A1 | 2/2004 | Yamada et al. | |
| 2006/0024638 A1 | 2/2006 | Rosenblood | |
| 2006/0146563 A1 * | 7/2006 | Chen | 362/561 |
| 2007/0230208 A1 * | 10/2007 | Plank et al. | 362/573 |

FOREIGN PATENT DOCUMENTS

| | | |
|---|---|---|
| DE | 101 25 340 A1 | 12/2002 |
| DE | 101 44 414 A1 | 3/2003 |
| EP | 0 879 582 A2 | 11/1998 |
| EP | 1 439 412 A1 | 7/2004 |
| GB | 2 182 802 A | 5/1987 |
| JP | 62-39081 | 2/1987 |
| JP | 2002-336275 | 11/2002 |
| WO | WO 00/67048 | 11/2000 |
| WO | WO 2005/022030 A2 | 3/2005 |

* cited by examiner

*Primary Examiner*—Anabel M Ton
(74) *Attorney, Agent, or Firm*—John C. Thompson; Alan S. Korman; Sandra J. Thompson

(57) ABSTRACT

A semiconductor radiation source, having at least two light sources which are fixed on a common base body and so light can be emitted gently over a total emission spectrum, the first light source having a short-wave, in particular from 400 to 430 nm emission spectrum, and the second light source having a longer-wave, in particular from approximately 450 to 480 nm emission spectrum. The first light source (16) is arranged in an optical axis (22) and the second light source (18) has at least two chips (24, 26, 28, 30) which are arranged in particular symmetrically with respect to one another and with respect to the optical axis (22) and in a manner surrounding the optical axis (22).

8 Claims, 5 Drawing Sheets

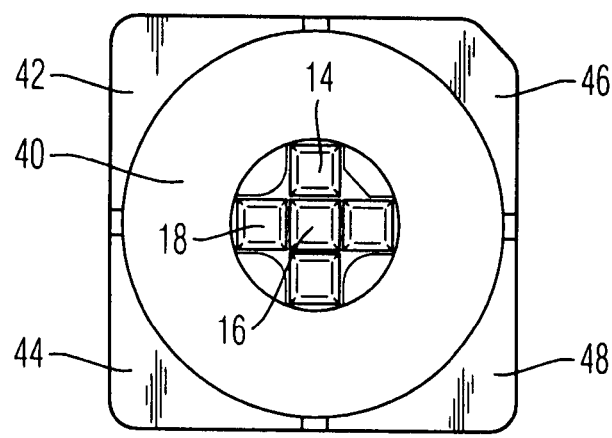
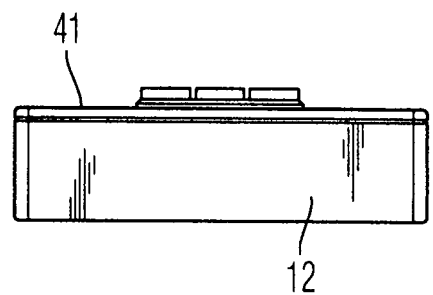
Fig. 5    Fig. 6
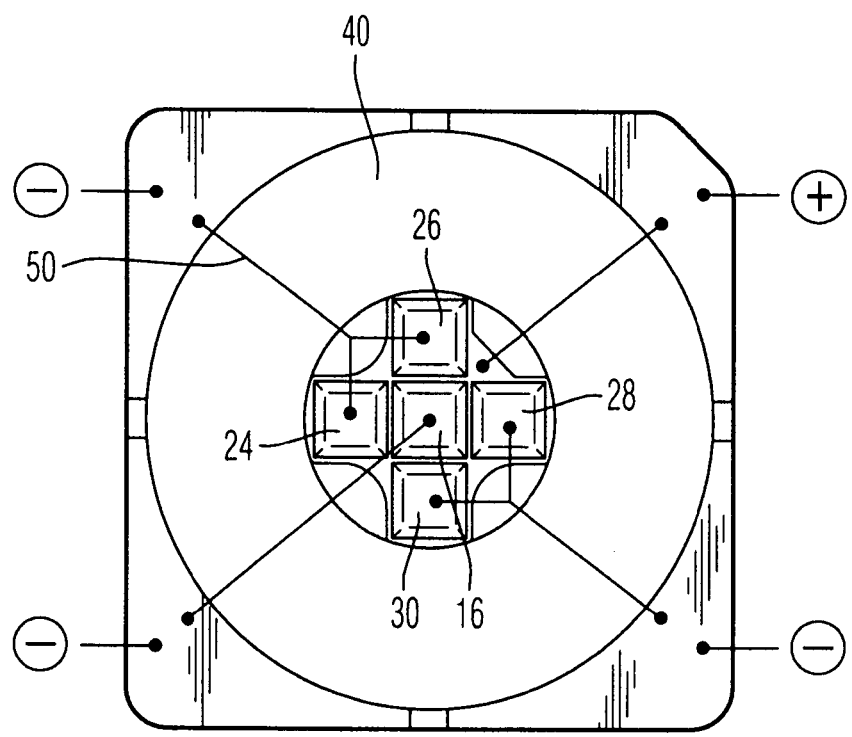
Fig. 7

SEMICONDUCTOR RADIATION SOURCE

CROSS-REFERENCE TO RELATED APPLICATIONS

This application claims foreign priority benefits under 35 U.S.C. §119 from German patent application Ser. No. 10 2006 015 336.7 filed Apr. 3, 2006.

TECHNICAL FIELD

The present invention relates to a semiconductor radiation source which may be used as a light curing device, and more particularly to such a device which includes at least two light sources which are fixed on a common base body and by means of which light can be emitted gently over differing emission spectrums.

BACKGROUND OF THE INVENTION

It has been known for a long time to have a radiation source using groups of light sources which emit light having different wavelengths, see for example from U.S. Pat. No. 4,568,558 and also EP 879 582. In the case of the first-mentioned solution, dental material is intended firstly to be partly polymerized with a wavelength of between 400 and 450 nm and subsequently to be completely polymerized with a wavelength of 350 nm. By contrast, LED chips having various wavelengths such as 435, 450 and 470 nm are intended to be used in the case of the second-mentioned solution.

The LEDs are arranged in bundled fashion and are uniformly supplied with voltage, with the result that selective driving is not possible. Different photoinitiators having different spectral sensitivities cannot be taken into account with this solution.

In the last 10 years numerous investigations have been undertaken in order to improve the effectiveness of the photopolymerization, in order to enable shorter treatment cycles for the dentist or, if appropriate, the dental technician without jeopardizing the reliability of the dental restoration upon full curing.

Accordingly, various photopolymerizable materials have been investigated and used, there generally having been the tendency to realize a greatest possible spectral overlap between the emission spectra of the light sources used and the sensitivity spectra of the photoiniators used. This of course necessitates the use of different spectral emission spectra which have been striven for in different photoinitiators.

Recently, so-called dual-curing systems have also been proposed, the solution in accordance with U.S. Pat. No. 6,866,506 enabling the curing result to be significantly improved. This solution provides two semiconductor radiation sources having different emission maxima which are spaced apart from one another and are each, in particular, at different points in time.

In the case of this solution, however, a multiplicity of chips is used for providing the light power, so that this solution is more likely to be considered for high-quality light curing devices. In order to provide the desired curing, use is made of chips having high light emission which are comparatively expensive, moreover, and which emit an intensive light radiation. This is all the more so since, in the case of this solution, the curing is performed by a respective group of chips successively, so that a subgroup of the chips must also have a power sufficient for the curing.

OBJECTS AND SUMMARY OF THE INVENTION

Against this background the invention is based on the object of providing a radiation source which can be used universally, is comparatively cost-effective to produce, but nevertheless enables a good radiation efficiency.

The invention provides for the light sources to be divided into two light sources, both light sources, which may each comprise a plurality of chips, being arranged in a central region of a common base body. The light sources therefore occupy only a very small portion—for example 10% or 15% or even just 5%—of the surface of the base body.

The invention provides for the first light source to be arranged in an optical axis and the second light source to have at least two chips which are arranged in particular symmetrically with respect to one another and with respect to the optical axis and in a manner surrounding the optical axis.

This surprisingly leads to a markedly high luminous efficiency in comparison with the previous solutions. By dispensing with a multiplicity of light sources that are rather arranged peripherally, the luminous efficiency can be significantly increased with corresponding converging lenses. This means that a significantly higher optical radiation can be emitted for the same introduced electrical energy. This effect is reinforced by the fact that a base body which is large in relation to the chip area is available when the peripheral chips are dispensed with, said base body accordingly acting as a cold buffer. The heat dissipation is therefore particularly high, precisely also during pulsed operation, so that the chips can basically be operated in the full-load range or even in the overload range without their service life being impaired.

The invention provides for all the chips to be arranged near the optical axis. A first light source is arranged in the optical axis, and a second light source is arranged in a manner surrounding the latter and closely adjacent to the latter.

The second light source is preferably arranged symmetrically, and it goes without saying that at least two chips are required for this symmetrical arrangement. Preferably, the second light source can be formed from four chips each arranged along an edge of the square central chip, to be precise with a smallest possible gap between the individual chips.

Overall, this produces a cross comprising the first light source as central chip and the four chips of the second light source, which surround the chip of the first light source in a manner adjoining it.

This surprisingly enables the luminous efficiency to be significantly increased, and it goes without saying that any suitable means can be used, that is to say for example a covering lens that covers the chips and concentrates emerging light, and also, if appropriate, a converging lens, which enables further focusing of the emitted light radiation.

On account of the small dimensions of the chips overall it is also possible, however, to act directly upon the introduction end of an optical waveguide.

It is particularly expedient according to the invention that as a result of dividing the light emission between two light sources, it is possible to excite photoinitiators in light-curing compositions in any suitable manner. By way of example, the first light source may be designed for the excitation of Lucerin in the wavelength range of 400 to 430 nm and the second light source may be designed for the excitation of camphorquinone for the wavelength range of between 450 and 480 nm.

When using dental compositions with both photoinitiators, it is then possible for both light sources to be switched on jointly, while it is also possible for each light source to be switched on separately depending on the material used.

In a particularly expedient refinement, the radiation source according to the invention can be used multifunctionally, that it to say not only as a light curing device, but also as an illumination device, in particular also for inspecting whether or not there are tooth gaps given the presence of plastic fillings in the patient's mouth.

A handheld device shaped in the manner of a handheld light curing device is particularly well suited to this because, by virtue of the usually fixed optical waveguide and the slender form, the light source can be directly introduced into the patient's mouth in a targeted manner and the illumination can be performed there without glare.

Preferably, for inspecting the edge gap situation, only one of the light sources, for example the first, weaker light source, is switched on in order that no glare effect arises. In this context, it goes without saying that the inspection wavelength can also be adapted to the requirements within wide ranges; it is preferably the shorter wavelength emitted by the first light source, which lies in the optical axis.

A further advantageous refinement provides for the second light source to have four chips which are arranged in the manner of a cross around the first light source, and for the first light source to have one chip.

A further advantageous refinement provides for the light sources to closely adjoin one another, the width of the gap that remains between them amounting to less than one fifth, in particular approximately one tenth, of the diameter of each chip. The gap width is preferably 0.5 to 2 mm, and in particular approximately 1 mm.

A further advantageous refinement provides for the first and second light sources to be arranged in a central region of the base body.

A further advantageous refinement provides for at least the first light source, in particular all the light sources, to be arranged in a central projection, in particular having a height of between 0.1 and 1 mm, of the base body.

A further advantageous refinement provides for the form of the projection to follow that of the light sources, and in particular essentially to have the form of a cross.

A further advantageous refinement provides for the light sources to be fixed on the base body or the projection by means of an adhesive bonding connection or by means of a soldering connection.

A further advantageous refinement provides for the base body and/or the projection to have a thermal conductivity which is better than 0.5 C/W.

A further advantageous refinement provides for the base body and/or the projection to be electrically conductive.

A further advantageous refinement provides for the base body to at least partly comprise copper.

A further advantageous refinement provides for the base body to be at least partly coated with gold or nickel-gold.

A further advantageous refinement provides for a printed circuit board to be arranged in a manner surrounding a central region, in particular the projection, of the base body, said printed circuit board carrying electrical connection contacts.

A further advantageous refinement provides for electrical connection contacts for the light sources to be arranged as zones on the outer periphery of the base body, in particular on a printed circuit board, and for bonding wires to extend from the chips to the electrical connection contacts.

A further advantageous refinement provides for the light sources to be covered by a convex covering lens, which is formed in plane fashion in particular on the side facing the light sources.

A further advantageous refinement provides for a spacer supported on the printed circuit board, in particular, to surround the light sources, and for the spacer together with the covering lens, in particular, to form a closed space in front of the light sources.

A further advantageous refinement provides for the closed space to have a liquid or viscous substance, in particular silicone gel, or a potting composition.

A further advantageous refinement provides for an optical element extending in front of the light sources, in particular the covering lens or a composition extending in front of the light sources, to have phosphorus particles.

A further advantageous refinement provides for a converging lens to be arranged in front of the light sources, at a distance of a multiple of the diameter thereof, in particular in front of the covering lens.

A further advantageous refinement provides for the covering lens to have a significantly larger diameter than the light sources and for a converging lens to have a significantly larger diameter than the covering lens, the diameter ratios in each case lying between 1.2:1 and 10:1, in particular.

A further advantageous refinement provides for an optical waveguide to be arranged in the optical axis of the semiconductor radiation source, in particular downstream of the converging lens in the radiation direction.

A further advantageous refinement provides for the first and second light source to be able to be switched on jointly.

A further advantageous refinement provides for the first and second light sources to be able to be switched on or switched off at different points in time.

A further advantageous refinement provides for illumination and optical detection of edge gaps in the case of plastic fillings in or on teeth, in particular by means of the switching on of the first light source.

A further advantageous refinement provides for an essentially annular spacer to support the covering lens at least partly on the printed circuit board and/or the base body and to surround the LED chips.

A further advantageous refinement provides for the spacer to have a conical or parabolic section on its side facing the LED chips.

A further advantageous refinement provides for a reflector to be arranged downstream of the covering lens in the beam path.

A further advantageous refinement provides for a reflector to support a converging lens arranged downstream of the covering lens in the beam path.

BRIEF DESCRIPTION OF THE FIGURES

Further advantages, details and features of the invention emerge from the following description of a plurality of exemplary embodiments of the invention with reference to the drawing, in which:

FIG. 5 shows a further embodiment of a radiation source according to the invention in plan view;

FIG. 6 shows the embodiment in accordance with FIG. 5 in side view;

FIG. 7 shows the embodiment in accordance with FIGS. 5 and 6 in an enlarged illustration;

DETAILED DESCRIPTION

Figure 1:
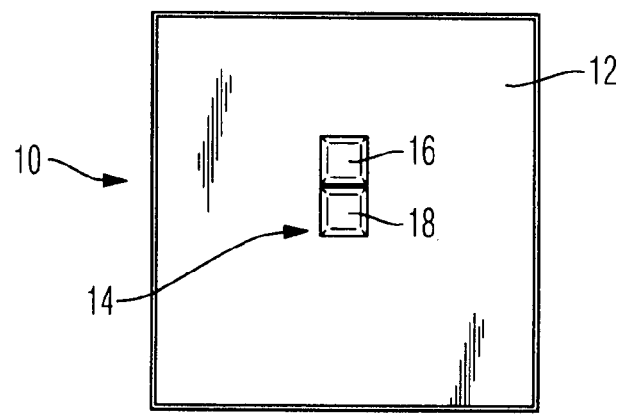
FIG. 1 shows a first schematic embodiment of a radiation source according to the invention in plan view.

FIG. 1 shows a semiconductor radiation source 10 in schematic plan view. A base body 12 is provided, which carries two chips in a central region 14. In this case, a first light source 16 is provided, which is arranged in an optical axis. In this exemplary embodiment, both light sources 16 and 18 are arranged directly in the central region of the base body 12 on which they are mounted, and which simultaneously serves for dissipating the heat generated by the chips. In this exemplary embodiment, the two chips are in each case arranged in a manner directly adjoining the optical axis 22. They have a gap 20 between them, which is kept as small as is technically and electrically possible in order to avoid short circuits, in which case the distance may be a few micrometers.

Each chip is formed in square fashion in a manner known per se.

Figure 2:
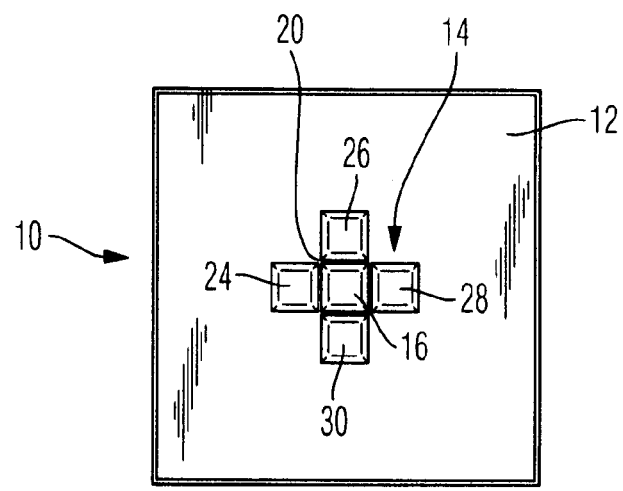
FIG. 2 shows a second embodiment of a radiation source according to the invention likewise in plan view.

A further embodiment of the semiconductor radiation source 10 according to the invention can be seen from FIG. 2. Here and also in the further FIGS., identical reference symbols denote identical or corresponding elements. In the exemplary embodiment in accordance with FIG. 2, the first light source 16 is provided directly in the optical axis 22. The second light source 16 comprises four chips 24, 26, 28 and 30 arranged in cruciform fashion around the chip of the first light source 18. All the chips have the same dimensions, so that the edge lengths correspond to one another. Markedly narrow gaps 20 are again provided, which enable electrical isolation but do not influence the spatial proximity of all the chips in the central region 14.

In this case, too, the first and second light sources 16 and 18 can be switched independently of one another and occupy the central region 14 of the base body 12, a significantly larger region remaining free.

Figures 3, 4:
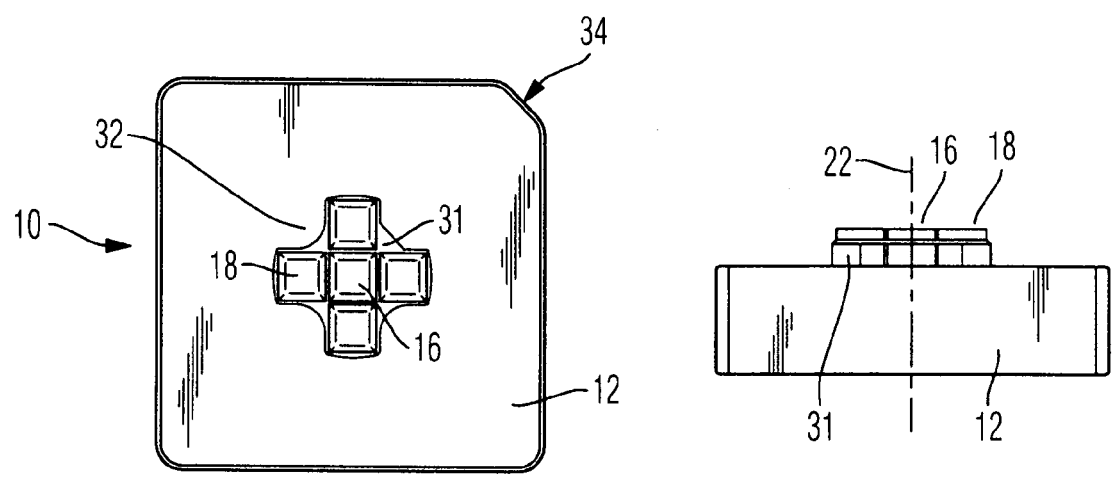
FIG. 3 shows a further embodiment of a radiation source according to the invention in plan view.
FIG. 4 shows the embodiment in accordance with FIG. 3 in side view.

A further embodiment of a radiation source 10 according to the invention can be seen from FIG. 3. In the case of this embodiment, which is illustrated in side view in FIG. 4, a projection 31 is provided, which carries the first and second light sources 16 and 18. The form of the projection 31 follows the cross formed by the first and second light sources 16 and 18, the junctions of the limbs at 32 each having radii and in this respect being somewhat rounded and enlarged. This enables simplified mounting of the chips onto the base body 12 and good heat dissipation from the chips to said base body.

The base body 12 preferably essentially comprises copper and is coated with a nickel-gold layer in particular on its front side, that is to say adjacent to the light sources. In modified refinement, the base body is completely coated with said layer on the outside.

It can be seen from FIG. 3 that the base body 12 has a bevel 34 at one corner. The bevel 34 serves to facilitate mounting in order to ensure that the contact areas discussed with reference to the subsequent FIGS. are connected correctly.

It can be seen from FIG. 4 that the thickness of the chips is significantly smaller than the thickness of the base body, for example by a factor of 10.

Moreover, the thickness of the chips for the light sources 16 and 18 is also somewhat smaller than the height of the projection 31.

FIG. 5 shows that the central region 14 may be surrounded by a ring area 40, which is preferably formed by a printed circuit board 41 bearing on the base body 12. An annulus fitted into the essentially square form of the base body 12 is preferably formed.

It is particularly expedient that four contact zones 42, 44, 46 and 48 spaced apart from one another are formed on the other side of the ring area 40. The contact zones 42 to 48 serve for making contact with connection wires or bonding wires for the chips of the light sources 16, 18. Accordingly, the bonding wires (also cf. FIG. 7) extend across the ring area 40. This also benefits the concentration of the light emission on the actually important central region 14.

It can be seen from FIG. 6 that the printed circuit board 41 can extend essentially at the same height as the projection 31. It goes without saying that a height adaptation can be performed in an arbitrary manner, so that the printed circuit board or the projection may also be thicker.

In this embodiment, series resistors are additionally provided for the LED chips, and a series resistor 49 can be seen from FIG. 6. With these series resistors, their calibration can be performed when LED chips are connected in parallel, so that it is also possible to use unsorted LED chips, which are cost-effective.

The way in which the bonding wires 50 extend for making contact with the individual chips can be seen from FIG. 7. The corresponding contact-making ensures separate driving of the chips 24 to 30 on the one hand, and of the light source 16, on the other hand.

It goes without saying that the electrical insulation of the chips 24 to 30 and of the chip of the light source 16 can be realized in a manner known per se, for example by means of a corresponding oxidation layer of the semiconductor material used. This is not in conflict with the fact that the chips can be securely fixed on the projection 31 or the base body 12.

It can be seen from FIG. 7 that a spacer 40 can surround the central region 14. The spacer 40 may be formed from plastid or light metal, for example, and protect the light sources 16 and 18. In the exemplary embodiment illustrated, it is annular and provided for receiving the covering lens 52 that can be seen from FIGS. 10 and 11.

Figure 8:
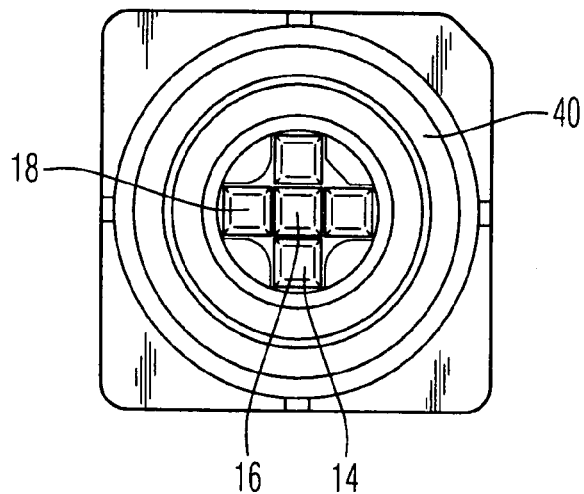
FIG. 8 shows a further embodiment of the radiation source according to the invention in plan view; per se.
Figure 9:
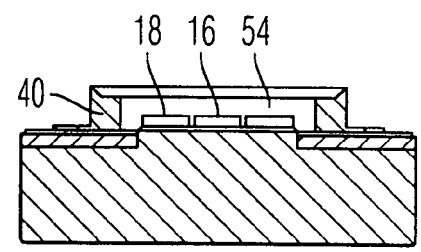
FIG. 9 shows the embodiment in accordance with FIG. 8 in side section.
Figure 10:
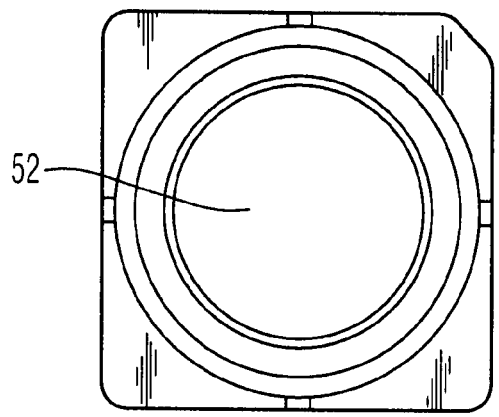
FIG. 10 shows a further embodiment of a radiation source according to the invention in plan view.
Figure 11:
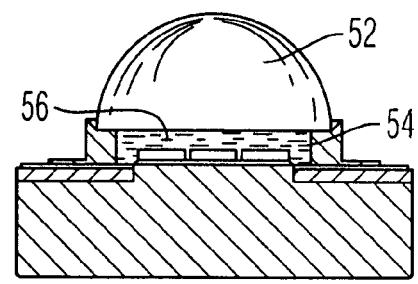
FIG. 11 shows the embodiment in accordance with FIG. 10 in lateral section.

Whereas in the embodiment in accordance with FIGS. 8 and 9, a space 54 remains above the light sources 16 and 18, this space 54 is closed and filled with a particular substance in the embodiment in accordance with FIGS. 10 and 11. In the exemplary embodiment illustrated, silicone gel 56 provided with yellow phosphorus particles is provided for this purpose. This ensures that the emitted light acquires a higher proportion of white without the light power being appreciably impaired.

Figure 12:
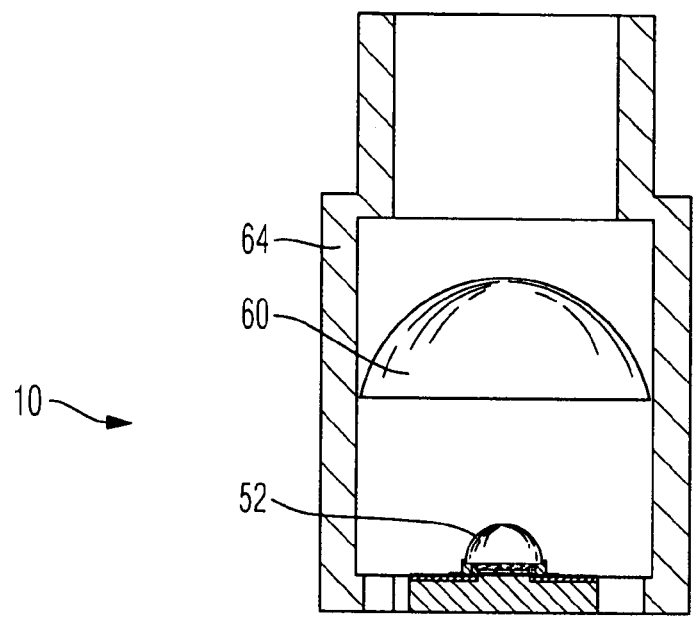
FIG. 12 shows a further embodiment of a radiation source according to the invention in lateral section.
Figure 13:
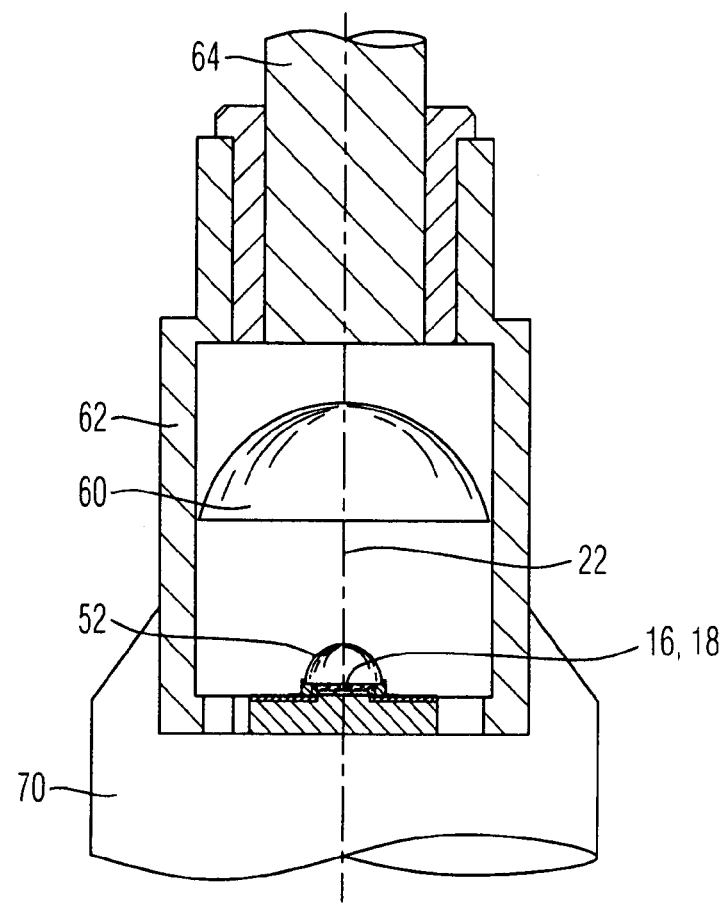
FIG. 13 shows a further embodiment of a radiation source according to the invention in lateral section.

In a particularly preferred refinement which can be seen from FIG. 12 and in modified form from FIG. 13, the radiation source according to the invention is incorporated into a partially illustrated combined illumination and light curing device. For this purpose, a converging lens 60 is provided, which is mounted by means of an optical holder 62 in such a way that it extends above the covering lens 52, to be precise in a manner overlapping and covering the latter. In the embodiment in accordance with FIG. 13, an optical waveguide 64 extends in the radiation direction adjacent to the converging lens 60. The light curing device, as indicated schematically in FIG. 13 has a housing 70 and is formed as a hand held device.

As can be seen from FIGS. 12 and 13, the light sources 16, 18 and also the covering lens 52, but also the converging lens 60 and the optical waveguide 64 are arranged along the optical axis 22. This enables a particularly good yield and easy focusing on the desired focal point.

Figure 14:
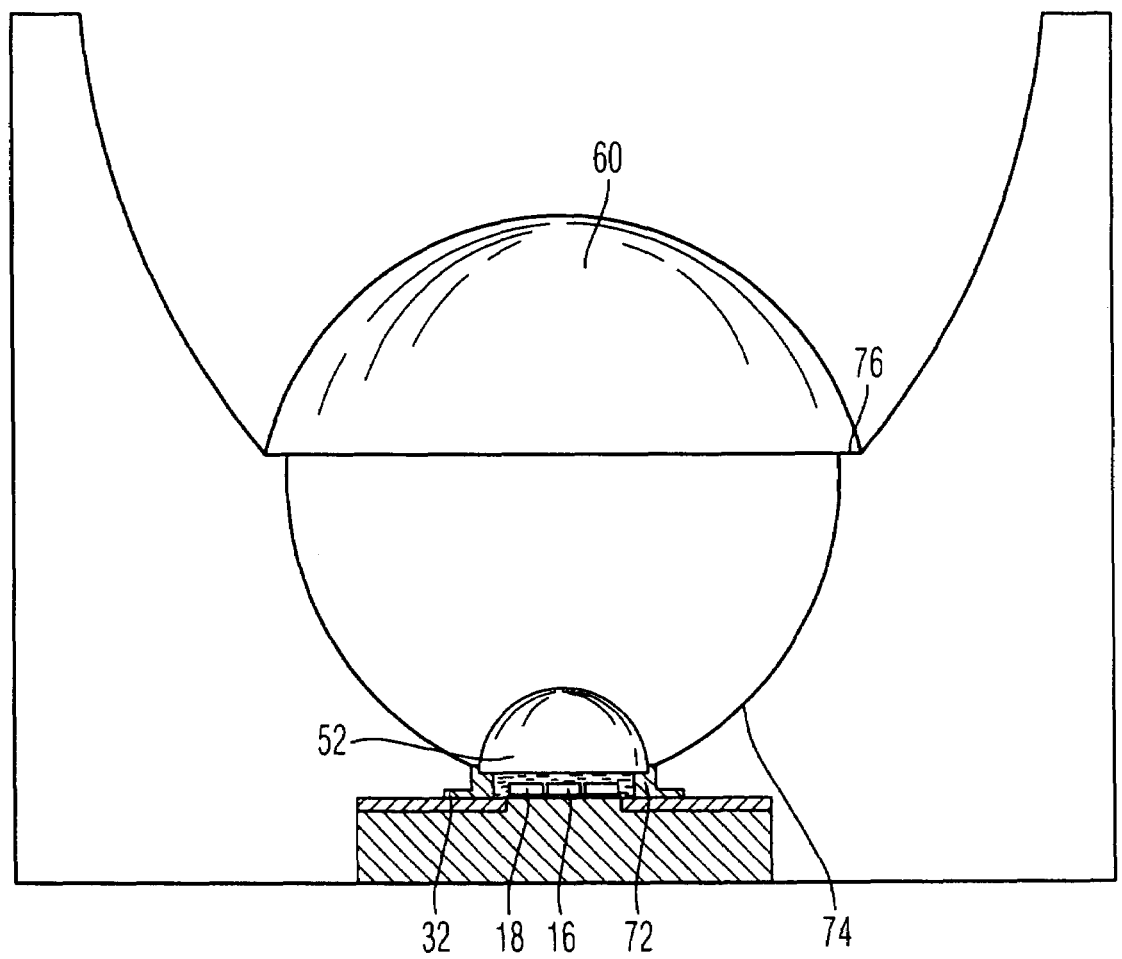
FIG. 14 shows a further embodiment of a radiation source according to the invention.

FIG. 14 shows a further embodiment of a radiation source according to the invention. In this embodiment, the LED chips 16, 18 are surrounded by a spacer 72, which simultaneously serves for supporting the covering lens 52. Adjacent to the spacer 72 there is a reflector 74, which expands parabolically and simultaneously forms a support for the converging lens 60 at a shoulder 76. Adjacent to the converging lens, the reflector 74 further extends parabolically or conically obliquely outward in order thus to ensure optimum concentration of the emitted light.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A semiconductor radiation source for curing light-polymerizable dental materials, said source comprising:
a common base body;
at least two light sources which are fixed on the common base body and by means of which light can be emitted jointly over a total emission spectrum,
the first light source having a short-wave, in particular from 400 to 430 nm emission spectrum, and
the second light source having a longer-wave, in particular from approximately 450 to 480 nm emission spectrum,
wherein one of the light sources (16), in particular the first light source, is arranged in an optical axis (22) and the other light source (18), in particular the second light source, has at least two chips (24, 26, 28, 30) which are arranged in particular symmetrically with respect to one another and with respect to the optical axis (22) and in a manner surrounding the optical axis (22), wherein a covering lens (52) is arranged in the beam path downstream of the LED chips (24, 26, 28, 30), said covering lens being formed in plane fashion in particular on the side facing the light sources, and wherein a spacer therefor is formed essentially in tubular or linear fashion, and wherein the spacer is at least partly supported on a printed circuit board and/or the base body (12), and wherein a closed space having a transparent or translucent, liquid or gelatinous substance, in particular silicone gel or a potting composition, extends between the LED chips (24, 26, 28, 30), the spacer and the covering lens.

2. The radiation source as claimed in claim 1, wherein the substance has phosphorus particles.

3. The radiation source as claimed in claim 1, wherein a converging lens is arranged in the beam path downstream of a covering lens, the diameter of said converging lens being, in particular, greater than the diameter of the covering lens.

4. The radiation source as claimed in claim 1, wherein a reflector is arranged at a distance from the LED chips (24, 26, 28, 30) in front of the latter, that is to say downstream of the latter in the beam.

5. The radiation source as claimed in claim 3, wherein the covering lens (52) has a significantly larger diameter than the light sources (16, 18), and the converging lens (60) has a significantly larger diameter than the covering lens (52), the diameter ratios respectively lying between 1.2:1 and 10:1.

6. The radiation source as claimed in claim 1, wherein the first and second light sources can be switched on jointly or at different points in time and/or can be switched off jointly or at different points in time.

7. A semiconductor radiation source for curing light-polymerizable dental materials, said source comprising:
a common base body;
at least two light sources which are fixed on the common base body and by means of which light can be emitted jointly over a total emission spectrum,
the first light source having a short-wave, in particular from 400 to 430 nm emission spectrum, and
the second light source having a longer-wave, in particular from approximately 450 to 480 nm emission spectrum,
wherein one of the light sources (16), in particular the first light source, is arranged in an optical axis (22) and the other light source (18), in particular the second light source, has at least two chips (24, 26, 28, 30) which are arranged in particular symmetrically with respect to one another and with respect to the optical axis (22) and in a manner surrounding the optical axis (22), wherein a covering lens (52) is arranged in the beam path downstream of the LED chips (24, 26, 28, 30), said covering lens being formed in plane fashion in particular on the side facing the light sources, and wherein a spacer therefor is formed essentially in tubular or linear fashion, and wherein the spacer is at least partly supported on a printed circuit board and/or the base body (12), and* wherein an essentially annular spacer supports the covering lens at least partly on the printed circuit board and/or the base body and surrounds the LED chips, and wherein a reflector is arranged in the beam path downstream of the covering lens.

8. The radiation source as claimed in claim 7, wherein the spacer has a conical or parabolic section on its side facing the LED chips.

* * * * *